United States Patent

Heid et al.

[11] Patent Number: 5,974,811
[45] Date of Patent: Nov. 2, 1999

[54] SUCTION DEVICE FOR CUTTING WASTES IN A CRYOSTATIC MICROTOME

[75] Inventors: Hans Heid, Bammental; Dieter Teppke, Schwetzingen, both of Germany

[73] Assignee: Carl-Zeiss-Stiftung trading as Carl Zeiss, Germany

[21] Appl. No.: 09/027,551

[22] Filed: Feb. 21, 1998

[30] Foreign Application Priority Data

Mar. 7, 1997 [DE] Germany ............................ 197 09 482

[51] Int. Cl.⁶ ...................................................... B26D 7/18
[52] U.S. Cl. ................................. 62/78; 62/320; 83/915.5
[58] Field of Search .............................. 62/320, 51.1, 78; 83/915.5

[56] References Cited

U.S. PATENT DOCUMENTS 5,255,585  10/1993  Gordon .
5,628,197  5/1997  Rada .................................. 83/915.5 X
5,740,708  4/1998  Tabone ................................ 83/915.5 X

FOREIGN PATENT DOCUMENTS

WO 94/28390  12/1994  WIPO .
WO 96/05495  2/1996  WIPO .

OTHER PUBLICATIONS

U.S. application No. 08/692,647, Jakobi et al., filed Aug. 1, 1996 Corresponds to German Application 195 28 180.2.

Primary Examiner—Christopher B. Kilner

[57] ABSTRACT

The suction device according to the invention for cryostatic microtomes has a filter for the separation of cutting wastes from the suction air stream, and a device arranged following the filter for sterilization or disinfection of the suction air stream. For this purpose, the air stream is first heated and then exposed to a strong UV irradiation. In the subsequent two-stage cooling arrangement, the air stream is cooled down again to about the cryostat temperature and is conducted back into the cryostat. The filter for the separation of the cutting wastes from the air stream is preferably constructed outside the cryostat as a liquid container with a disinfecting liquid, so that the cutting wastes are disinfected in the disinfecting liquid. A contamination of the surroundings or of the internal space of the cryostat with disease germs is largely prevented.

11 Claims, 1 Drawing Sheet

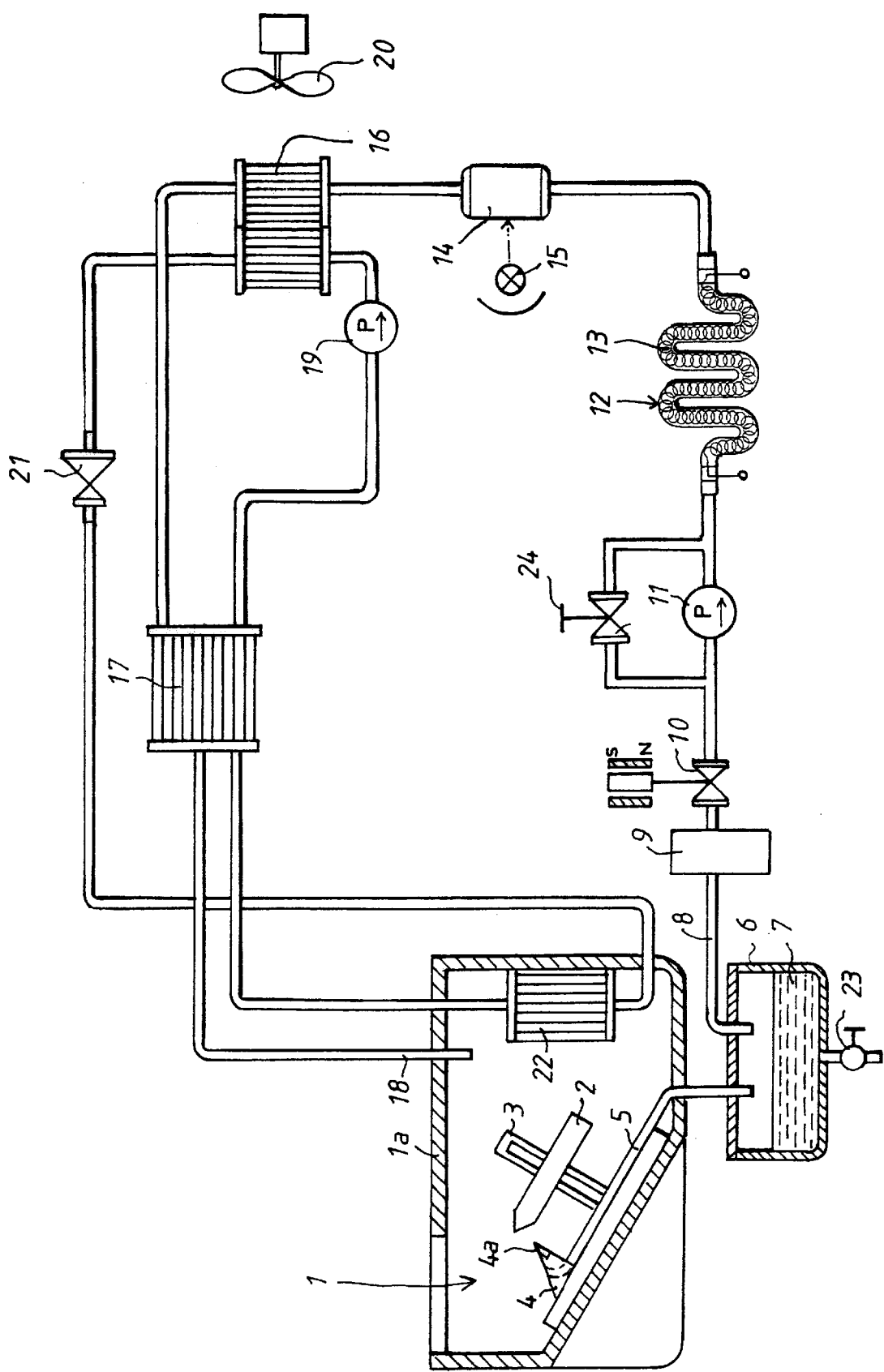

SUCTION DEVICE FOR CUTTING WASTES IN A CRYOSTATIC MICROTOME

BACKGROUND OF THE INVENTION

1. Field of the Invention

This invention relates to a suction device for cutting wastes in a cryostatic microtome, and more particularly to an arrangement for disinfecting and sterilizing the air stream of the suction device.

2. Discussion of Relevant Prior Art

A suction device for cryostatic microtomes is known from U.S. Pat. No. 5,255,585, in which at least a first filter is arranged in the internal space of the cryostat. The cutting wastes arising during cutting are trapped by this first filter and are stored in the frozen state, corresponding to the cryostat temperature, at temperatures in the region between −10° C. and −40° C. A bacteriological filter can optionally be connected after this filter, to retain microscopic particles which pass through the first filter, before the exhaust air of the suction device is delivered to the atmosphere. It is a disadvantage in this system that substantially warmer outside air is permanently exchanged for the cooled air in the cryostat. To maintain a stable cryostat temperature, in particular in the low temperature region, a considerable cooling power of the cryostat is therefore required.

It is furthermore disadvantageous that the air delivered from the suction device into the surroundings is in fact filtered and is also partially freed from bacteria by the use of a bacteriological filter, but nevertheless an effective disinfection of the exhaust air cannot be attained by mechanical cleaning.

A further suction device for cryostatic microtomes is offered by Microm Laborgeräte GmbH under the name "Vacutome". This suction device has, inside the cryostat, a container with a paper filter to trap the cutting waste. In contrast to U.S. Pat. No. 5,255,585, this suction device works according to the principle of circulation, i.e., after mechanical cleaning by the paper filter, the air stream of the suction device is conducted back into the cryostat. A large introduction of outside air into the cryostat is thereby avoided. However, in this case also, a complete, or nearly complete, sterilization of the air stream does not take place. Thus contamination of the air in the cryostat, and hence an enrichment of the specimen to be cut with disease sources, can take place here. Apart from this, contaminated air is also released to the surroundings on opening the cryostat.

SUMMARY OF THE INVENTION

The present invention has as its object a suction device for cutting waste in a cryostatic microtome, in which both a contamination of the surroundings of the cryostat with possible disease sources which are present in the specimen to be cut, and also an enrichment with disease sources of the specimen to be cut, are largely prevented.

This object is attained by means of a suction device for cutting wastes in a cryostatic microtome, wherein there are successively arranged in the air stream of the suction device a filter for separating the air stream from the cutting wastes and, after the filter, a device for disinfection and sterilization of the air.

The suction device according to the invention has a filter to separate the air stream from the cutting wastes, and a device arranged after this filter for the disinfection and sterilization of the air within the air stream of the suction device. A heating device can for example be provided for sterilization, to heat the air stream of the suction device to temperatures which kill germs. Alternatively or additionally, the air stream of the suction device can also be exposed to a germicidal irradiation, for example, an electromagnetic irradiation in the wavelength region under 300 nm.

The filter for the separation of the cutting wastes from the air stream of the suction device is preferably constructed as a container to receive a disinfecting liquid. The air stream of the suction device is then conducted into the container, or out of the container, above the liquid level provided. The aspirated suction wastes fall into the disinfection liquid in this arrangement, so that in the case of a possible contamination of the cutting wastes with disease germs, these are killed in the disinfection liquid. The cutting wastes can therefore be sucked out when required, together with the disinfection solution.

The liquid container is preferably arranged outside the internal space of the cryostat. The space requirement within the cryostat is thereby reduced, and in addition disinfection liquids whose freezing point is above the working temperature of the cryostat can be used without any problems.

In principle, the air which has been freed from cutting residues and sterilized can be delivered without problems to the surroundings, as in U.S. Pat. No. 5,255,585 mentioned at the beginning. However, it is preferred to conduct the air back into the cryostat after being freed from cutting wastes and after disinfection, in order to reduce the subsequent flow of warmer outside air into the cryostat. In such a system which operates according to the principle of circulation, a gas filter for the separation of the vapors of the disinfecting liquid from the air should be provided in the air stream of the suction device, before the return of the air stream into the cryostat. This prevents vapors of the disinfecting liquid getting into the cryostat, where they could deposit in liquid or solid form and impair the operation of the microtome, or could affect the health of the operators. Furthermore, a heat exchanger should be provided for cooling the air stream down again before it is returned into the cryostat.

In a cryostatic microtome with a suction device according to the invention, the filter, the device for disinfection and sterilization of the air stream, and also one or more successive heat exchangers for cooling the air stream down again, can thus all be arranged outside the cryostat.

BRIEF DESCRIPTION OF THE DRAWING

Details of the invention are further described hereinbelow with reference to the flow diagram of principles, shown in the FIGURE, of an embodiment of the invention.

DETAILED DESCRIPTION OF A PREFERRED EMBODIMENT

The cryostat shown in the FIGURE has a thermally insulating wall (1a) and a cryostat internal space (1) which is cooled, in contrast to the temperature of the surroundings, to working temperatures between −10° C. and −40° C. A conventional cooling system, further detailed below, is used for the cooling of the cryostat.

The microtome, indicated only schematically here by the knife holder (4) and the specimen carrier which is movable along a linear guideway (3), is arranged within the internal space (1) of the cryostat. For sectioning, the specimen carrier (2) is moved along the linear guideway (3) and thus conducted over a cutting knife clamped in the knife holder (4) with its knife edge perpendicular to the plane of the drawing. The microtome itself can be constructed, for example, corresponding to International Patent Document WO 96/05495, or to the German Patent Application DE 19528180.2 of Microm Laborgeräte GmbH.

For the aspiration of the cutting wastes, a conduit (5) is provided in the region of the base of the microtome, and is connected to a bore within the knife holder (4). The bore within the knife holder (4) opens at the back face (4a), inclined forward, of the cutting knife. A corresponding knife holder is known from International Patent Document WO 94/28390, which should be consulted for specific details of the construction of the knife holder (4).

The other end of the conduit (5) is led out of the internal space (1) of the cryostat, without the interposition of other components, and opens from above into an airtightly closed container. The container is filled with a disinfecting liquid (7), with the conduit (5) opening into the container (6) above the level of the liquid. Formaldehyde, glutaraldehyde, peracetic acid, hydrogen peroxide, bleach solutions, or ethanol or propanol solutions which are over 70%, are possible candidates as suitable disinfecting solutions. A further suction tube (8) opens into the container (6) above the surface of the disinfecting liquid. This further suction tube (8) is connected via a gas filter (9) and a magnetic valve (10) to the suction side of a pump (11). When the pump (11) is in operation, a reduced pressure is thereby produced in the container (6) and conduit (5), and the sections produced on the microtome and lying on the back side (4a) of the knife holder (4) are sucked out. The aspirated sections are transported through the conduit 5 by the reduced pressure and, on emerging from the mouth end of the conduit (5), fall into the disinfecting liquid (7) within the container (6). The cutting wastes are thereby bound in the disinfecting liquid (7), and can be disposed of together with the disinfecting liquid (7), which is let out together with the cutting wastes through an outlet valve (23) in the floor of the container (6). Alternatively, in particular when no outlet valve is present on the container (6), the container (6) can be separated form the conduit (5) and from the suction tube (8), and can then be removed for emptying.

The air stream sucked out of the container (6) is enriched with gases of the disinfecting liquid. The vapors of the disinfecting liquid are separated from the air by the gas filter (9), for example an adsorption filter containing active carbon as the filtering material, and the vapors of the disinfecting liquid are thus trapped in the gas filter (9).

The pressure side of the pump (11) is first connected to a thermal disinfection device. This consists of a glass tube (12), into which is inserted a helically bent heating coil (13), for example of steel or constantan wire. The two ends of the heating coil (13) are led out of the glass tube and connected to a current source (not shown). The heating coil is heated to about 200° C. by the current through the heating coil (13), so that the air transported through the glass tube (12) is heated to a temperature which is suitable for killing the germs and viruses present in the air. Corresponding temperatures of the air stream are, for example, about 100° C.

The glass tube (12) is bent helically or in a meandering form, so that with a compact arrangement the glass tube (12) is long enough for the heating of the air.

A second sterilization step follows the thermal disinfection, for safety reasons. In this second sterilization step, the air stream is exposed to a germicidal electromagnetic irradiation. A quartz glass bulb (14) is provided for this purpose; the air stream is passed through it. The quartz glass bulb (14) is irradiated from outside by a UV irradiator with a light wavelength of less than 254 nm, so that sterilization by irradiation takes place. By the use of a UV light wavelength of less than 200 nm, a portion of the air within the quartz glass bulb (14) is converted into ozone, so that an additional chemical poisoning takes place of any disease germs which may still be present in the air stream.

After passing through the described two-stage sterilization device, the air stream is cooled down again, in one or more heat exchangers (16, 17) which effect cooling, to a temperature which about corresponds to the temperature in the internal space of the cryostat, and is then conducted back to the internal space of the cryostat via a conduit (18). The heat exchangers (16, 17) for cooling the air stream are thus connected to the cooling circuit of the cryostat. The cooling circuit of the cryostat has a conventional construction, with a compressor (19), a heat exchanger (16) arranged at the pressure side of the compressor (19), and a throttle (21) connected following the heat exchanger (16). The gaseous coolant compressed by the compressor (19) is cooled in the heat exchanger (16), by the outside air blown by a fan (20), to the liquefaction temperature, giving up heat to the surroundings. The cooled coolant passes through the throttle (21) and expands in a heat exchanger (22) in the internal space (1) of the cryostat, the internal space (1) being thereby cooled to the desired operating temperature. After leaving this heat exchanger (22), the coolant passes through the heat exchanger (17) for the cooling of the air stream of the suction device, and in fact in a counter-current process such that the coolant of the heat exchanger (17) passes through in a direction opposite to the direction of motion of the air stream of the suction device. After leaving the heat exchanger (17), the warmed coolant is again compressed in the compressor (19) and is again cooled in the heat exchanger (16) for the next cycle. By the inclusion of the cooling down of the suction air stream in the coolant circuit which already exists for the cryostat, only a simple heat exchanger (17) and a double heat exchanger (16) are required in addition, so that the additional cost for the cooling down of the suction air stream is relatively small. The double heat exchanger (16) then effects a cooling of the air stream of the suction device to about the ambient temperature, and the simple heat exchanger (17), to about cryostat temperature.

A bypass (24) is connected in parallel to the pump (11), connecting the inlet side and outlet side of the pump together. The air stream can circulate through this bypass (24) when the magnetic valve (10) is closed.

The magnetic valve (10) serves for the relief of the cooling system. For this purpose, the magnetic valve (10) is connected, via an electronic control which is not shown, to the motion of the specimen carrier (2), such that the magnetic valve (10) is opened when the specimen to be cut is located just above the knife edge, and is closed again when the specimen has completely passed the knife edge and the section has consequently been taken off. The switching time points for the opening and closing of the magnetic valve are adjustable according to the size of the specimen. A corresponding electronic control is already known from the suction device offered by Microm Laborgeräte GmbH under the name "Vacutome", and therefore does not need to be described in detail in this place.

We claim:

1. A suction device for cutting wastes in a cryostatic microtome, comprising, successively arranged in an air stream of said suction device:

a filter for separating said air stream from cutting wastes, and a device (12, 13, 14, 15) that disinfects and sterilizes said air stream, following said filter (6).

2. The suction device according to claim 1, wherein said filter comprises a container (6) that receives a disinfecting liquid (7), in which said air stream is introduced into said container (6) above a level of said disinfecting liquid (7).

3. The suction device according to claim 2, further comprising a gas filter (9) that separates vapors of said disinfecting liquid (7) in said air stream sucked from said container (6).

4. The suction device according to claim (2), wherein said container (6) is arranged outside an internal space of a cryostat.

5. The suction device according to claim 4, wherein said air stream, after separation of cutting wastes and after passage through said device that disinfects and sterilizes (12, 13, 14, 15), is fed back into said internal space of said cryostat.

6. The suction device according to claim 1, in which said device that disinfects and sterilizes said air stream includes a device that heats said air stream to a germicidal temperature for sterilization.

7. The suction device according to claim 6, wherein said device that heats said air stream comprises a glass tube (12) and a heating coil (13) inserted in said glass tube.

8. The suction device according to claim (6), further comprising a cooling down device (16, 17) that cools down said air stream before said air stream returns to said internal space of said cryostat.

9. The suction device according to claim 1, further comprising at least one of a source of UV irradiation or another short wavelength electromagnetic irradiation to which said air stream is exposed for sterilization.

10. The suction device according to claim 1 in combination with a cryostatic microtome with a cryostat compartment having a cryostat internal space (1), a cooling device (19, 16, 21, 22), and a microtome having a specimen holder (2) and a knife holder (4) arranged in said cryostat compartment.

11. The combination according to claim 10, in which said filter (6), said device that disinfects and sterilizes (12, 13, 14, 15) said air stream, and at least one successively arranged heat exchanger (16, 17) for cooling said air stream down, are arranged outside said internal space (1) of said cryostat.

* * * * *